(12) United States Patent
Roesler et al.

(10) Patent No.: US 8,778,989 B2
(45) Date of Patent: Jul. 15, 2014

(54) COSMETIC COMPOSITION COMPRISING A LIPID FRACTION FROM VEGETABLE SOURCE AND ANTICRYSTALING AGENT

(75) Inventors: Roberta Roesler, Sao Paulo (BR); Rosa Friedlander, Sao Paulo (BR)

(73) Assignee: Natura Cosmeticos S.A., Sao Paulo—SP (BR)

( * ) Notice: Subject to any disclaimer, the term of this patent is extended or adjusted under 35 U.S.C. 154(b) by 1577 days.

(21) Appl. No.: 11/571,475

(22) PCT Filed: Jul. 1, 2005

(86) PCT No.: PCT/IB2005/001907
§ 371 (c)(1),
(2), (4) Date: Dec. 11, 2007

(87) PCT Pub. No.: WO2006/006047
PCT Pub. Date: Jan. 19, 2006

(65) Prior Publication Data
US 2008/0188551 A1    Aug. 7, 2008

(30) Foreign Application Priority Data
Jul. 2, 2004 (BR) ...................................... 0402633

(51) Int. Cl.
*A61K 31/355* (2006.01)
(52) U.S. Cl.
USPC .......................................... 514/458; 514/474
(58) Field of Classification Search
CPC ... A61K 31/355; C07C 31/125; B01J 31/063; C04B 24/085
USPC .......................................... 514/458, 474, 558
See application file for complete search history.

(56) References Cited

U.S. PATENT DOCUMENTS

| | | | |
|---|---|---|---|
| 3,502,594 A | 3/1970 | Ahrens | |
| 4,181,634 A * | 1/1980 | Kennedy et al. | 510/122 |
| 4,534,981 A | 8/1985 | Zabotto et al. | |
| 5,660,865 A | 8/1997 | Pedersen et al. | |
| 6,165,453 A | 12/2000 | Buheitel | |
| 2003/0068426 A1 * | 4/2003 | Idris et al. | 426/601 |
| 2003/0143312 A1 | 7/2003 | Tamarkin et al. | |
| 2004/0241254 A1 * | 12/2004 | Kopas et al. | 424/727 |

FOREIGN PATENT DOCUMENTS

EP    0 556 995    8/1993

OTHER PUBLICATIONS

International Search Report for PCT Application No. PCT/IB2005/0019074; filed Jul. 1, 2005; Date of Completion Nov. 3, 2005; Date of Mailing Nov. 10, 2005.
PCT International Preliminary Examination Reportfor PCT Application No. PCT/IB2005/001907; filed Jul. 1, 2005; Date of Submission of the Demand May 2, 2006; Date of Completion Dec. 6, 2006.
International Search Report and Written Opinion for PCT Application No. PCT/IB2005/001907; filed Jul. 1, 2005.

* cited by examiner

*Primary Examiner* — Jason Sims
*Assistant Examiner* — Ibrahim D Bori
(74) *Attorney, Agent, or Firm* — Alston & Bird LLP

(57) ABSTRACT

The present invention relates to a cosmetic composition comprising: a—from 85.0% to 99.9% by weight of a lipid fraction of vegetable origin, and b—from 0.1% to 15.0% by weight of an anti-crystallizing agent, the percentages being defined on the basis of the total weight of the composition. The present invention also relates to a cosmetic composition comprising olein, propoxylated stearyl alcohol and/or propoxilated stearyl ether. These cosmetic compositions are ecologically correct and exhibit high resistance to oxidation and to solidification, and further provide to the skin softness, lubrication and also brings about the formation of a film that protects the skin against drying out.

11 Claims, No Drawings

12; # COSMETIC COMPOSITION COMPRISING A LIPID FRACTION FROM VEGETABLE SOURCE AND ANTICRYSTALING AGENT

This application claims the priority of Brazilian patent case No. PI0402633-0 filed on Jul. 2, 2004 which is hereby incorporated by reference.

FIELD OF THE INVENTION

The present invention relates to a cosmetic composition that comprises a vegetable oily base and imparts softness, lubrication to the skin, and further brings about the formation of a film that protects the skin against drying out.

BACKGROUND OF THE INVENTION

Mineral oil, derived from exhaustible natural reserves, is usually employed as a base for bath oils and massage oils, as well as other cosmetics known in the prior art. This application is due mainly to the low cost, safety, availability and emollience foreseen in said oil, which is constituted by a mixture of hydrocarbons obtained from a rigorous purification of the fractions of petroleum distillates.

At present, the use of fossil fuels is considered a serious threat to the atmosphere and to the environment, since the burning thereof emits large amounts of polluting gases and carbon dioxide. Additionally, it is estimated that between 40 and 60 years, natural gas and oil will exhaust worldwide.

Thus, the need to find alternatives that will minimize or replace fossil fuels is vital, due to exhaustion of their reserves or to pollution of the environment and of the atmosphere caused by the burning thereof.

Vegetable oils are a promising alternative for replacing mineral oil used in bath oil and massage oil, since they have many properties and varieties to be exploited, such as high concentration of essential fatty acids, natural moisturizing function and emollience, besides comprising natural bioactives (phytosterols, vitamins, minerals, antioxidants, among others).

The use of oils on the skin began in ancient times as a religious practice, especially in the consecration of priests and kings. The origin of the application of lipids onto the skin goes back to over two millenniums, when they were believed to have benefits in terms of appearance and health of the skin, as well as a barrier against the environment. Cosmetic use of natural oils and fats, which are instable (they oxidize easily) and difficult to emulsify, would not have become so popular if they did not present so many physical benefits, such as emollience, lubrication, moisturizing and occlusiveness, as well as biochemical benefits such as the possible restoration of the damaged skin barrier provided by them. Source: Y. Huy, Bayles Industrial Oil and Fat Products, vol. 5).

Studies and clinical tests aimed overcoming drying-out of the skin are based on the concept that an oily surface or a lipid film would delay the loss of water by evaporation. The importance of bath oils for dry skins is thus explained. Bath oil needs to be applied onto the skin so as to form a thin film and cover as much surface area as possible, without, however, making it oily, and this aspect would be non-attractive to the consumer. The spreadability of the oil should be satisfactory, since said oil should provide a thin film on the skin. A rapid spreading is important, since the area covered by the oil is proportional to its spreadability, and an oil that spread rapidly is considered more attractive for cosmetic reasons (Source: Wilkinsons J. B. and Moore R. J., Harry's Cosmeticology).

At present, the production of body-care products that exhibit emollient properties of vegetable oils is particularly desirable. Vegetable oils can be as emollient as mineral oils and some of them can be even better. In general, vegetable oils do not have the same barrier as mineral oils, since they are polar substances. However, they are capable of penetrating deeper into the horny layer (stratum corneum), which explains the great contribution in terms of softness of these oils. Further, the barrier formed by mineral oils provides reduction of the transsepidemic loss of water and the increase of the moisture of the epidermis, but does not moisturize the skin in an ideal way. From this point of view, the low barrier formed by vegetable oils is considered a benefit. Other reasons for using vegetable oils are the presence of an active ingredient that has physiological function, as well as the fact that unsaturated fatty acids can have beneficial effects for the skin (Source: Connock E., 1998, Cosmetics and Toiletries).

On the other hand, vegetable oils that are in liquid state at room temperature and that comprise a high concentration of unsaturated fatty acids are rapidly oxidized when exposed to the environment (an effect caused by light, temperature and oxygen), which changes the color and odor of the oil, besides entailing the formation of free radicals that cause damages to the cells of the skin and renders the product unacceptable for this use.

The applicant indicates hereinafter relevant documents of the prior art related to the matter of the present invention.

Document U.S. Pat. No. 5,318,777 describes a solvent-extraction process for obtaining an olein with 0% of solids at 20° C. and 4.5% of solids at 10° C., as well as the cosmetic application thereof. The profile of solids of the olein obtained by said process is not suitable for replacing mineral oil in cosmetic products, mainly when it comes to products with a large percentage of this raw material such as emulsions, bath oils and massage oils, among others. This can be verified in the fact that, while carrying out the process, olein will be subjected to a temperature of 10° C. This measure will initiate the formation of crystals with subsequent solidification of the cosmetic product that comprises said olein. This factor is extremely negative and generally associated to quality problems.

Additionally, extraction by solvent is a non-ecologically correct technique, since there may be a contamination of the environment or exhaustion of the natural resources necessary for obtaining the solvents. In this case, the use of hexane is cited, which is obtained from a mineral resource that is expected to exhaust in a few years.

Document U.S. Pat. No. 5,653,988 describes the manufacture of bath oil with 55% of surfactant and 45% of triglycerides. The oils indicated for being used in the compositions foreseen in this document, as for example, soybean oil and/or sunflower oil, have low resistance to oxidation, due to the high concentration of polyunsaturated fatty acids, which makes the product highly susceptible to degradation with the consequent formation of free radicals and unpleasant odor. Due to the possible degradation that this composition would undergo, the addition of antioxidants becomes compulsory and represents a very high cost for the product in question.

Additionally, the high amount of surfactants makes the final product more irritating than the bath oils already known.

Therefore, an objective of the present invention is to provide a vegetable-oil-based cosmetic composition that has advantages preferable to resistance to oxidation and to solidification related to lower financial costs, besides providing excellent cosmetic properties foreseen in the composition of the present invention.

SUMMARY OF THE INVENTION

The present invention refers to a cosmetic composition comprising:
a—from 85.0% to 99.9% by weight of a lipid fraction of vegetable origin and
b—from 0.1% to 15.0% by weight of an anti-crystallizing agent, the percentages being defined on the basis of the total weight of the composition.

The present invention also relates to a cosmetic composition comprising olein, propoxylated stearate and/or propoxylated stearyl ether.

DETAILED DESCRIPTION OF THE INVENTION

The present invention describes an oily cosmetic composition comprising a lipid fraction of vegetable origin having high resistance to oxidation and an anti-crystallizing agent that, in turn, imparts high resistance to solidification. In addition to these components already cited, it may also contain at least one antioxidant agent, auxiliary components and actives that provide the desired characteristics.

The main objective that has led to the development of this cosmetic composition was that of replacing, in an excellent way, the use of mineral oils in cosmetic and/or dermatologic product. Thus, it can be concluded that this composition is ecologically correct, since it does not cause any impact on the environment, such as exhaustion of non-renewable resources such as petroleum. Additionally, the achieved formation provides to softness and lubrication to the skin, as well as a film that covers it, thus preventing it from drying out.

The cosmetic composition of the present composition can serve as a basis for various cosmetic products marketed, and may contain some type of active principle for the skin, for instance. The amount of the cosmetic composition of the invention comprised in said cosmetic product ranges from 20% to 99% by weight, based on the total weight of the cosmetic product. The main examples of products that can be prepared from the cosmetic composition of the present invention are:
Monophasic bath oil;
Biphasic bath oil;
Triphasic bath oil; and
Body emulsion.

The present invention has various advantages over compositions of the prior art, a few of them being cited below.
the cosmetic composition of the present invention comprises only components of sustainable (vegetable) origin. Thus, it is an ecologically correct composition, replacing the use of mineral oils derived from petroleum, without cause any losses with regard to its properties;
the combination between the adequate lipid fraction and the anti-crystallizing agent provide softness, lubrication and further provides the formation of a protective film over the skin so as to prevent it from drying out;
by virtue of the lipid fraction present in the constitution of the present invention, the cosmetic composition is highly resistant to both oxidation and solidification, and so it is not compulsory to add antioxidant agents in large amounts;
by virtue of the optional addition of antioxidant agents in smaller amounts than those found in compositions of the prior art, the present invention has financial advantages, since it is more economical to produce; and
as can be seen from the tests presented hereinafter, the cosmetic composition of the present invention has guarantee of dermatological safety, since no potential for photoirritation and/or photosensitization, primary or accumulated dermal irritation and comedogenic potential was found.

Lipid Fraction

The preferred triglyceride to be used as a lipid fraction in the present invention is palm olein. Alternatively, in association with palm olein, other oils of vegetable origin can be added such as, for example, cottonseed oil, Para-nut oil, carap-nut oil, maracock oil, etc.

Preferably triglycerides of vegetable origin that exhibit high resistance to oxidation are used in the present invention. As already known, oxidation may be defined as the deterioration that is organoleptically detectable in oils and fats and is the most important phenomenon of degradation of these compounds. As will be explained later, the resistance of triglycerides to oxidation is identified through the values of theoretical reactivity. The smaller the value of the theoretical reactivity, the higher the resistance to oxidation and, consequently, the greater its stability. Therefore, for the present invention, the triglycerides contained in the cosmetic composition described herein are limited to those that exhibit a low theoretical reactivity.

Further, some factors favor oxidation, as for instance, contact with oxygen, the presence of traces of metals in the oils, excess energy (temperature and light), formation of free radicals by means of antioxidants, among others.

It is also known that the velocity of oxidation reaction is determined by the distribution, geometry and number of double bonds. A methylene ($-CH_2-$) between two double bonds is a very active center of oxidation. The high reactivity of the group of methylene isolated from 9,12-linoleic acid is responsible for the fact that this fatty acid and its esters oxidize 15 times as fast as oleic acid which does not have this methylene group. Linolenic acid, which contains two activated methylene groups, oxidizes 2 as fast as linoleic acid (Source: D. Swern, Bayley's Industrial Oil and Fat Products).

A table showing the velocities of oxidation of the main fatty acids found in vegetable oils is given below.

TABLE 03

Relative Velocity of Oxidation of Fatty Acids

| Fatty acid | T = 100° C. | T = 40° C. | T = 20° C. | T = 37° C. |
|---|---|---|---|---|
| Stearic | 0.6 | — | — | — |
| Oleic | 6 | — | 4 | — |
| Linoleic | 64 | — | 48 | 42 |
| Linolenic | 100 | 100 | 100 | 100 |

In this regard, it can be noticed that the evaluation of the fatty composition of the oil or derivative is a very important factor for obtaining a vegetable base that is more resistant to oxidation, since the smaller the concentration of polyunsaturated fatty acids such as linoleic acid and linolenic acid, the better the resistance of the cosmetic composition to oxidation. Since one of the objectives of the present invention is to provide a cosmetic composition that is resistant to oxidation, the first step was to identify an oily base that already comprises this property.

To justify the preference for the use of palm olein as the lipidic function comprised in the cosmetic composition of the present invention, a comparative table is given below, relating to the fatty compositions of cosmetic compositions that comprise vegetable oils such as soybean oil, sunflower oil, canola oil, maize oil and cottonseed oil, in addition to the cosmetic composition of the present invention, which comprises, in its preferred embodiment, palm oil.

|  | Sunflower | Canola | Maize | Soybean | Cotton | Palm |
|---|---|---|---|---|---|---|
| FATTY DISTRIBUTION | | | | | | |
| C12:0 | — | — | — | — | 0.21 | 0.4 |
| C14:0 | 0.5 | 0.2 | 0.1 | 0.5 | 0.78 | 1.0 |
| C16:0 | 3.0-10.0 | 2.5-6.5 | 9.0-14.0 | 7.0-14.0 | 24.3 | 35.8 |
| C18:0 | 1.0-10.0 | 0.8-3.0 | 0.5-4.0 | 1.4-5.5 | 1.77 | 4.4 |
| C18:1 | 14.0-35.0 | 53.0-70.0 | 24.0-42.0 | 19.0-30.0 | 15.-73 | 47.0 |
| C18:2 | 55.0-75.0 | 15.0-30.0 | 34.0-62.0 | 44.0-62.0 | 57.18 | 11.0 |
| C18:3 | 0.8 | 5.0-13.0 | 2.0 | 4.0-11.0 | — | 0.4 |
| C20:0 | 1.5 | 0.1-1.2 | 1.0 | 1.0 | 0.03 | 0.3 |
| C20:1 | 0.5 | 0.1-4.3 | 0.5 | 1.0 | — | — |
| C22:0 | 1.0 | 0.6 | 0.5 | 0.5 | — | — |
| C22:1 | 0.5 | 2.0 | — | 0.2 | — | — |
| THEORETICAL REACTIVITY | | | | | | |
|  | 38.2 | 30.2 | 33.4 | 42 | 28.1 | 7.6 |

The theoretical reactivity is calculated as being the weighted average of the theoretical reactivities of oleic, linoleic and linolenic fatty acids, as reproduced in the above table.

Therefore, it can be seen that the vegetable oil has greater resistance to oxidation. This evidence has been further confirmed by carrying out a study of resistance to oxidation defined later, designated as Test 3.

Especially with regard to palm olein, this substance acts on the cosmetic composition of the present invention as a carrier, an equivalent function of the vegetable oil present in the cosmetic compositions of the prior art, and further as emollient. Moreover, palm olein provides the properties of softness, lubrication and formation of a protective film over the skin upon application of the product.

In the preferred embodiments, as lipidic function, palm olein is added in an amount of at least 85% by weight, preferably varying around 95% by weight, based on the total weight of the composition.

In alternative embodiments, it is possible to use an amount ranging from 75% to 85% of palm olein in the constitution of the cosmetic composition of the present invention. However, the best results achieved with respect to the properties and advantages already listed before are related to the compositions that comprise at least 85% by weight of lipid fraction.

The palm olein mentioned above is a lipid fraction achieved preferably in accordance with the steps shown below.

Physical cold weighing of the pulp of the palm fruit, *Elaeis guineensis*;

Distillation of the oil obtained in order to remove the undesirable components such as free fatty acids and peroxides, and Fractioning for obtaining the lipid fraction—olein.

Further, in order to obtain a differentiated olein, that is to say, an olein that exhibits resistance to solidification, it is indicated that the rationing step is carried out as follow:

the temperature is slowly and gradually reduced, preferably at a rate from 0.5 to 4.5° C./h. At the moment when a temperature of 9 to 13° C. is achieved, preferably 11° C., the component should remain at this temperature for a period ranging from 2 to 5 hours, so that the crystals formed can be strengthened. The crystallization consists, in general, of 3 stages: cooling, forming the core and growth of the crystals. Once the crystals have been formed, they do not remain isolated, but rather aggregate so as to form crystals of larger surface mass, resulting from small glyceride cores of high fusion weight;

the frequency of stirring is slowly and gradually reduced, during the crystallization process, until it reached a frequency between 8 and 16 rpm, preferably 9 rpm;

the filtration takes place when a temperature between 9 and 15° C., preferably 11° C., is reached.

Alternatively, the olein may be extracted by using a solvent in substitution for the fractioning process. However, since an essential characteristic of the present invention is to be ecologically correct, the fractioning is opted.

Anti-crystallizing Agent

At least one anti-crystallizing agent selected from: alcohol, ethoxylated alcohol such as ethyxylated cetyl alcohol, ethoxylated glycol polyethylene, propoxylated alcohol such as propoxylated cetyl alcohol, propoxylated stearyl alcohol, ethoxylated ether such as ethoxylated glyceryl cocoate, propoxylated ether such as propoxylated stearyl ether, hydrogenated and ethoxylated vegetable oils and others such as vegetable lipoprotein, sorbitol and combinations thereof.

In preferred embodiments, as an anti-crystallizing agent, propoxylated stearyl ether is added in an amount ranging from about 0.1% to about 25.0% by weight, preferably 0.1% to 15%, more preferably from about 3.0 to 5.0%, based on the total weight of the composition. The choice of the propoxylated stearyl ether is due to the result obtained by carrying out comparative tests, where different anti-crystallizing agents were added in compositions that comprised palm olein. This test is defined below (Test 6). The composition that comprised palm olein and propoxylated stearyl ether has exhibited better resistance to oxidation. Therefore, propoxylated stearyl ether has exhibited an unexpected property when in combination with palm olein, since it has made the composition resistant to the action of oxidation for a longer time.

This compound is the preferred one to be used in the cosmetic composition of the present invention, since in an amount of, for instance, only 5% by weight, based on the total weight of the composition, it provides an anti-crystallizing activity, delaying the formation of crystals of the lipidic fraction, even when the composition is exposed to cold. Further, since they are non-ionic surfactants, they are milder than others used ion compositions that contain vegetable oils of the prior art and still provide, together with the vegetable oil, softness and emollience. And since the amount of surfactant ion the composition of the present invention is low, it is not aggressive to the skin.

Moreover, it has been found, in studies, that propoxylated stearyl ether exhibits a synergistic effect over the freezing point of the olein extracted from palm oil (the preferred lipidic fraction of the present invention), and this effect is not found in other surfactants studied.

In addition to the above-mentioned components, the compositions of the invention may further comprise compounds that are conventionally used in cosmetic compositions and that will be detailed hereinafter.

Antioxidant Agent

Examples of preferred antioxidant agents to be added to the present invention are: natural antioxidant agents such as tocopherols (vitamin E), carotenoids (vitamin A), phenolic compounds (gallic acid, quercetin, catechin, chlorogenic acid), ascorbyl palmitate (vitamin C); and further synthetic antioxidant agents such as BHT, BHA, TBHQ or components that also act as sequestering agents such as a-hydroxy acids (citric acid, malic acid, lactic acid), EDTA, among others, as well as mixtures thereof.

In preferred embodiments, as an antioxidant agent, TBHQ is added in an amount ranging from about 0.01% to about 0.10% by weight, preferably from 0.03% to 0.07% by weight, more preferably about 0.5% by weight, based on the total weight of the composition.

Fragrance

In the cosmetic composition like the one described herein, it is optional to add perfume of fragrance selected from a variety of possible substances. The amount of fragrance to be added to the cosmetic compositions of the present invention preferably ranges from about 1.0% to about 10.0%, more preferably from about 4.0% to about 5.0% by weight, based on the total weight of the composition.

Other Optional Components

In order to impart to the cosmetic compositions of the present invention some desirable characteristic that is not achieved with the known components, other components that are compatible with those already present in it may be added. Some of these compounds that may be added to the composition are:

chelating agent such as etidronic acid, ethylenediaminotetraacetic acid (EDTA), sodium gluconate;

pH adjusting agent such as trietanolamine;

preserving agent such as sodium acetate, boric acid;

emollients such as soybean lecithin, isopropyl palmitate and vegetable squalene;

actives;

bacteriostatics, bactericides or antimicrobials;

stabilizing agents such as sodium chloride;

dyes;

carriers such as water;

other cosmetically accepted components that are compatible with the base composition.

Examples of Composition

The examples given below are preferred embodiments of the cosmetic compositions of the present invention and should not be interpreted as being limitative thereof. Thus, many other variations of composition may be carried out within the scope of protection delimited by the accompanying claims.

1 - Anhydrous monophasic bath oil with formation of emollient film

| Components | Mass amount (%) | | |
|---|---|---|---|
| | Example 1.1 | Example 1.2 | Example 1.3 |
| Vegetable oily base* | 80 | 70 | 60 |
| Soybean lecithin | 3 | 4 | 6 |
| Isopropyl palmitate** | 12 | 15 | 20 |
| Ethoxylated fatty alcohol | 0 | 3 | 5 |
| Preserving agent | q.s.p. | q.s.p. | q.s.p. |
| Antioxidant agent | q.s.p. | q.s.p. | q.s.p. |
| Fragrance | q.s.p. | q.s.p. | q.s.p. |

Notes:
*The constitution of the Vegetable Oily Base is: 94.95% of palm olein obtained from palms native of the state of Pará, Brazil, available from the company Agropalma, 5.00% of propoxylated stearyl ether and 0.05% TBHQ;
**The isopropyl palmitate compound may be combined with or replaced by vegetable squalene.

2 - Anhydrous monophasic bath oil with light sensorial

| Components | Mass amount (%) | | |
|---|---|---|---|
| | Example 2.1 | Example 2.2 | Example 2.3 |
| Vegetable oily base* | 85 | 75 | 60 |
| Dicaprylic ether** | 10 | 15 | 25 |
| Ethoxylated fatty alcohol | 0 | 3 | 5 |
| Preserving agent | q.s.p. | q.s.p. | q.s.p. |
| Antioxidant agent | q.s.p. | q.s.p. | q.s.p. |
| Fragrance | q.s.p. | q.s.p. | q.s.p. |

Notes:
*The constitution of the Vegetable Oily Base is: 94.95% of palm olein obtained from palms native of the state of Pará, Brazil, available from the company Agropalma, 5.00% of propoxylated stearyl ether and 0.05% TBHQ;
**The dicaprylic ether compound may be combined with or replaced by dicaprylyl carbonate and triglycerides of capric acid and caprylic acid.

3 - Biphasic bath oil

| Components | Mass amount (%) | | |
|---|---|---|---|
| | Example 3.1 | Example 3.2 | Example 3.3 |
| Vegetable oily base* | 25 | 35 | 45 |
| Water | 45 | 45 | 45 |
| Dicaprylic ether** | 20 | 10 | 0 |
| Ethoxylated fatty alcohol | 0 | 3 | 5 |
| Preserving agent | q.s.p. | q.s.p. | q.s.p. |
| Antioxidant agent | q.s.p. | q.s.p. | q.s.p. |
| Fragrance | q.s.p. | q.s.p. | q.s.p. |
| Dyes | q.s.p. | q.s.p. | q.s.p. |

Notes:
*The constitution of the Vegetable Oily Base is: 94.95% of palm olein obtained from palms native of the state of Pará, Brazil, available from the company Agropalma, 5.00% of propoxylated stearyl ether and 0.05% TBHQ;
**The dicaprylic ether compound may be combined with or replaced by dicaprylyl carbonate, triglycerides of capric acid and caprylic acid, isopropyl palmitate and vegetable squalene.

4 - Triphasic Oil

| Components | Mass amount (%) | | |
|---|---|---|---|
| | Example 4.1 | Example 4.2 | Example 4.3 |
| Demineralized water | 27 | 25 | 25 |
| Sodium chloride | 5 | 5 | 5 |
| Hexyleneglycol | 29 | 29 | 29 |
| Vegetable oily base | 29 | 20 | 10 |
| Dicaprylic ether** | 0 | 9 | 18 |
| Ethoxylated fatty alcohol | 0 | 3 | 4 |
| Preserving agent | q.s.p. | q.s.p. | q.s.p. |
| Antioxidant agent | q.s.p. | q.s.p. | q.s.p. |
| Fragrance | q.s.p. | q.s.p. | q.s.p. |
| Dyes | q.s.p. | q.s.p. | q.s.p. |

Notes:
*The constitution of the Vegetable Oily Base is: 94.95% of palm olein obtained from palms native of the state of Pará, Brazil, available from the company Agropalma, 5.00% of propoxylated stearyl ether and 0.05% TBHQ;
**The dicaprylic ether compound may be combined with or replaced by dicaprylyl carbonate, triglycerides of capric acid and caprylic acid, isopropyl palmitate and vegetable squalene.

| 5 - Oil-in-water body emulsion | | | |
|---|---|---|---|
| | Mass amount (%0) | | |
| Components | Example 5.1 | Example 5.2 | Example 5.3 |
| Demineralized water | 75 | 75 | 65 |
| Vegetable oily base* | 5 | 10 | 20 |
| Dicaprylic ether** | 5 | 0 | 0 |
| Thickening agent | 1 | 1 | 1 |
| Emulsifying agent | 9 | 9 | 9 |
| Preserving agent | q.s.p. | q.s.p. | q.s.p. |
| Antioxidant agent | q.s.p. | q.s.p. | q.s.p. |
| Fragrance | q.s.p. | q.s.p. | q.s.p. |
| Dyes | q.s.p. | q.s.p. | q.s.p. |

Notes:
*The constitution of the Vegetable Oily Base is: 94.95% of palm olein obtained from palms native of the state of Pará, Brazil, available from the company Agropalma, 5.00% of propoxylated stearyl ether and 0.05% TBHQ;
**The dicaprylic ether compound may be combined with or replaced by dicaprylyl carbonate, triglycerides of capric acid and caprylic acid, isopropyl palmitate and vegetable squalene.

Tests

Below, we present studies and tests that prove the characteristics and properties present in the cosmetic composition of the present invention:

1—Study of the percentage of solids in function of the temperature

This study indicates the relationship between the amount of solids existing in the composition and the change in temperature. Thus, one determines principally the resistance of the cosmetic composition of the present invention to solidification.

1—palm olein (based on the present invention);
2—cocoa olein (based on patent application WO 83/00418);
3—olein as described in patent application JP 81,127,694; and
4—olein as described in patent U.S. Pat. No. 5,318,777.

| Test 01 Curve of olein solids (%) at different temperatures | | | | |
|---|---|---|---|---|
| Temperature (° C.) | Product 1 (%) | Product 2 (%) | Product 3 (%) | Product 4 (%) |
| 0 | 4.7 | 53.6 | 41.5 | 27.5 |
| 10 | 0 | 43.6 | 14.0 | 2.7 |
| 20 | 0 | 21.0 | 1.5 | 0 |
| 20 | 0 | 1.8 | 0.2 | 0 |

From the data reproduced above, it can be seen clearly that the cosmetic composition of the present invention exhibits a significant advance with regard to the solidification of olein. Consequently, the product that comprises the cosmetic composition of the invention exhibits better quality, independently of the storage temperature, the product being anhydrous or emulsion.

2. Cold Test (Test at Low Temperatures)

By carrying out this test, the resistance of the lipidic components is measured when subjected to low temperatures. The test was carried out at a temperature of 5° C.

The compositions of the products mentioned in following table:

Product 1—cosmetic composition of the present invention—composition: 94.95% of palm olein available on the market; 5.00% of propoxylated stearyl ether and 0.05% of TBHQ;

Product 2—100% of palm olein available on the market.

In order to carry out this test, samples of the products 1 and 2 were heated until the temperature of 40° C. was reached, for a period of 1 hour. Then, they were subjected to a temperature of 5° C. From this moment on, it can be verified how long it will take for the crystallization to begin, that is to say, the formation of small visible crystals.

TABLE 02

| Resistance to cold (° C.) | |
|---|---|
| Product | Time for the crystallization to begin (hour) |
| Product 1 | 10-12 |
| Product 2 | 2-4 |

From the values found, it can be easily concluded that the cosmetic composition of the present invention exhibits much higher resistance to solidification than the cosmetic product commonly found on the market.

3—Study of Resistance to Oxidation—$2^{nd}$ Part: OSI and Racimat

Analytic studies were carried out for the purpose of finding the stability of oils and their lipidic fractions, as well as the efficiency of the antioxidants used. These studies were carried out by using equipment known in the art, such as Rancimat and OSI (Oil Stability Index) capable of detecting the induction period of oils and fats, that is to say, the moment when the resistance of the oil to oxidation is exceeded and from which oxidation occurs in a very rapidly.

At a temperature of 110° C. and at a flow of atmospheric air of 9 l/h, 5 samples of 5 g each of the products 1 and 2 were analyzed, the compositions of which are:

Product 1—100% of soybean oil available for consumption;
Product 2—100% of maize oil available for consumption;
Product 3—100% of canola oil available for consumption;
Product 4—100% of cottonseed oil available for consumption;
Product 5—100% of palm olein available for consumption.

TABLE 05

| Induction time of available vegetable oils | | |
|---|---|---|
| Vegetable oil | Induction time (h) - OSI | Theoretical reactivity |
| Soybean | 5.6 | 42.0 |
| Maize | 8.0 | 33.4 |
| Canola | 8.1 | 30.2 |
| Cotton | 19.2 | 28.1 |
| Palm | 26.7 | 7.6 |

From this test, it can be seen that the longer induction time for indicting the recorded time of useful life of the oils was for that of palm olein, and again one concludes for it resistance to oxidation.

After the initial evaluation of the resistance to oxidation (induction time) of the cosmetic composition of the present invention, which proved to be very superior to the other products, a study was made with different antioxidant agents, isolated and/or associated, as can be seen from the table below.

Product 1—100% of palm olein available on the market;
Product 2—composition: 99.9% of palm olein, 0.05% of BHT and 0.05% of BHA;
Product 3—composition: 98.9% of palm olein, 0.1% of ascorbyl and 1.0% of tocopherol;

Product 4—composition: 99.95% of palm olein and 0.05% of TBHQ; and

Product 5—composition: 99.9% of palm oil and 0.1% TBHQ.

TABLE 06

Efficacy of different antioxidant systems,
% of protection and estimated validity time

| Product | Induction time (h) | % Protection | Estimated validity 40° C. | 25° C. |
| --- | --- | --- | --- | --- |
| Product 1 | 22.6 | 0.0 | 4.0 | 11.4 |
| Product 2 | 27.8 | 16.8 | 4.9 | 14.0 |
| Product 3 | 58.0 | 152.4 | 10.3 | 29.2 |
| Product 4 | 71.3 | 213.3 | 12.7 | 35.8 |
| Product 5 | >88.0 | >286.6 | >15.6 | >44.2 |

From the results shown above, it can be noticed that it may be interesting to add at least one antioxidant agent to the cosmetic composition of the present invention in order to prolong its useful life.

4. Study of Sensorial Characteristics

Thus study relates to the evaluation of sensorial characteristics to find out the real possibility of replacement of the mineral oil commonly used in cosmetic products by the preferred vegetable oils to be added to the cosmetic composition of the present invention.

By "sensorial characteristics" in the present context, it can be understood these attributes: spreadability, softness, formation of film over the skin, oiliness and stickiness.

This study was carried out in laboratory with 56 users of bath oils, who evaluated the attributes listed above. In this tests, products 1 and 2 were analyzed, which are two preferred embodiments of the cosmetic composition of the present invention, and products 3 and 4, which are cosmetic composition known from the prior art and comprise mineral oil. The compositions of products 1 to 4 are:

Product 1—composition: 80% of mineral oil, 3% of soybean lecithin, 12% of isopropyl palmitate, preserving agent, antioxidant agent and fragrance;

Product 2—composition of example 1.1 of the present invention;

Product 3—composition: 27% of demineralized water, 5% of sodium chloride, 29% of hexyleneglycol, 29% of mineral oil, preserving agent, antioxidant agent, dyes and fragrance; and Product 4—composition of example 4.1 of the present invention.

The results collected in this study show that there is no significant difference with respect to the evaluated attributes or the preference of the volunteers.

5. Safety Test

Physical-chemical tests, in vitro tests, assays on animals and also on humans were carried out, in order to prevent any reaction on the part of the user in using the cosmetic composition of the present invention.

The tables below contain the results obtained in the evaluation of a preferred embodiment of the cosmetic composition of the present invention, the constitution of which is:

Product—composition: 94.95% of palm olein, 5.0% of propoxylated stearyl ether and 0.05% of TBHQ.

TABLE 07

Physical-Chemical Assays

| Assays | Results |
| --- | --- |
| Organochlorinate residues | <1.0 ug/kg |
| Aromatic polycyclic hydrocarbons | <50.0 ug/kg |

TABLE 08

Tests on Animals

| Tests | Result |
| --- | --- |
| Limit dose | DL 50 higher than 20.0 ml/kg |
| Ocular irritation OECD 405 | Slight irritation |
| Primary dermal irritation OECD 404 | Non-irritant |
| Maximized dermal irritation OECD 406 | Non-irritant |
| Cumulative dermal sensitization OECD 410 | Non-irritant |
| Photosensitivity | Did not evidence any photosensitizing potential |

TABLE 09

In Vitro Tests

| Tests | Results |
| --- | --- |
| Mutagenicity (Ames) | Negative for TA 98 and TA 100 *S. typhimurium* strains |
| Cytotoxicity | Exhibited toxic effect for cell lines NCTC Clone 929 |

TABLE 10

Assays on Human Beings

| Assays | Results |
| --- | --- |
| Photo-irritating and photosensitizing topic potential | No photo-irritating and/or photosensitizing potential observed |
| Test for topical compatibility | No potential for primary dermal irritation, potential for accumulated dermal irritation and/or dermal sensitization was observed |
| Comedogenicity | No comedogenic potential was observed |

Therefore, it can be concluded that the cosmetic composition of the present invention presents dermatologic safety guarantee, since no potential for photo-irritation and/or photosensitization, potential for primary or accumulated dermal irritation, dermal sensitization and comedogenic potential was found, being indicated for topical use of users of bath oils and body emulsions.

6. Comparative Tests

Tests were carried out by using palm olein as a selected lipidic fraction in combination with various anti-crystallizing agents, in order to compare their performance. The control composition contains 100% of olein. The other compositions contain different anti-crystallizing agents in the amounts specified in the table below, in addition to palm olein.

To carry out this test, the anti-crystallizing agents in the amounts discriminated below were added to the palm olein, and the mixtures were heated up to the temperature of 40° C. for 1 hour. Later, they were subjected to a temperature of 5° C. From this moment on, one verifies how long it will take for crystallization to begin, that it to say, the formation of small visible crystals.

The results are shown in the following table.

TABLE 11

Analysis of the crystallization of cosmetic compositions containing palm olein

| Composition | Anti-crystallizing agent | Amount (%) | Appearance of the mixture |
|---|---|---|---|
| 01 | PEG 200 | 3.0 | Cloudy |
| 02 | PEG 200 | 5.0 | Cloudy |
| 03 | PPG 15 (stearyl ether) | 3.0 | Limpid |
| 04 | PPG 15 (stearyl ether | 5.0 | Limpid |
| 05 | Propyleneglycol | 0.5 | A little cloudy |
| 06 | propyleneglycol | 1.0 | Very cloudy |
| 07 | Procetyl AWS | 3.0 | Limpid |
| 08 | Procetyl AWS | 5.0 | Limpid |
| 09 | Glycerox H | 3.0 | limpid |
| 10 | Glycerox H | 5.0 | A little cloudy |
| 11 | Control | — | Translucent |

| | Crystallization in hours | | | | |
|---|---|---|---|---|---|
| Composition | 1 | 2 | 3 | 4 | 5 |
| 01 | OK | OK | OK | MIST | Begin of crystallization |
| 02 | OK | OK | OK | OK | Begin of crystallization |
| 03 | OK | OK | OK | OK | Begin of crystallization |
| 04 | OK | OK | OK | OK | OK |
| 05 | OK | OK | OK | Mist | Average crystallization |
| 06 | OK | OK | OK | OK | Average crystallization |
| 07 | OK | OK | OK | OK | Mist |
| 08 | OK | OK | OK | OK | Mist |
| 09 | OK | OK | OK | OK | Mist |
| 10 | OK | OK | OK | Begin of crystallization | Average crystallization |
| 11 | OK | OK | OK | OK | Begin of crystallization |

| | Crystallization in hours | | | |
|---|---|---|---|---|
| Composition | 6 | 7 | 8 | 9 |
| 01 | Average crystallization | High crystallization | Solid | Solid |
| 02 | Average crystallization | High crystallization | Solid | Solid |
| 03 | Begin of crystallization | Begin of crystallization | Average crystallization | Solid |
| 04 | Mist | Begin of crystallization | Average crystallization | High crystallization |
| 05 | Average crystallization | High crystallization | Solid | Solid |
| 06 | Average crystallization | High crystallization | Solid | Solid |
| 07 | Begin of crystallization | Average crystallization | High crystallization | Solid |
| 08 | Begin crystallization | Average crystallization | Solid | Solid |
| 09 | Begin of crystallization | High crystallization | Solid | Solid |
| 10 | Begin of crystallization | Average crystallization | High crystallization | Solid |
| 11 | Begin of crystallization | Average crystallization | High crystallization | solid |

In the face of these results, as already said in item "Anti-crystallizing agent", it can be concluded that propoxylated stearyl ether is the most suitable anti-crystallizing agent to be used in cosmetic compositions containing palm olein as an oily base. The association between palm olein and propoxylated stearyl ether has exhibited the longest interval of time for solidification (about 9 hours). So, it can be verified that this association is the one most resistant to solidification.

The invention claimed is:

1. A cosmetic composition comprising:
   a—from 85.0% to 99.9% by weight of palm olein, and
   b—from 0.1% to 15.0% by weight of an anti-crystallizing agent selected from the group consisting of propoxylated stearyl alcohol, propoxylated stearyl ether and a combination thereof.

2. A cosmetic composition according to claim 1, characterized by comprising 95% by weight of palm olein.

3. A cosmetic composition according to claim 1, characterized by comprising from 3.0% about 5.0% by weight of the anti-crystallizing agent.

4. A cosmetic composition according to claim 1, characterized by comprising an anti-oxidant agent.

5. A cosmetic composition according to claim 4, characterized in that the antioxidant agent is selected from the group consisting of natural antioxidant agents such as tocopherols (vitamin E), carotenoids (vitamin A), phenolic compounds (gallic acid, quercatin, catechin, chlorogenic acid), ascorbyl palmitate (vitamin C), BHT, BHA, TBHQ, a-hydroxy acids (citric acid, malic acid, lactic acid), EDTA and mixtures thereof.

6. A cosmetic product characterized by comprising the cosmetic composition as defined in claim 1.

7. A cosmetic product according to claim 6, characterized in that the amount of cosmetic composition ranges from 20% to 99% by weight, based on the total weight of the cosmetic product.

8. A cosmetic product characterized by comprising the cosmetic composition as defined in claim 2.

9. A cosmetic product characterized by comprising the cosmetic composition as defined in claim 3.

10. A cosmetic product characterized by comprising the cosmetic composition as defined in claim 4.

11. A cosmetic product characterized by comprising the cosmetic composition as defined in claim 5.

* * * * *

UNITED STATES PATENT AND TRADEMARK OFFICE
CERTIFICATE OF CORRECTION

| | | |
|---|---|---|
| PATENT NO. | : 8,778,989 B2 | Page 1 of 1 |
| APPLICATION NO. | : 11/571475 | |
| DATED | : July 15, 2014 | |
| INVENTOR(S) | : Roesler et al. | |

It is certified that error appears in the above-identified patent and that said Letters Patent is hereby corrected as shown below:

On the Title page, Item [54] and in the Specification, Column 1, lines 1-3,
"COSMETIC COMPOSITION COMPRISING A LIPID FRACTION FROM VEGETABLE SOURCE AND ANTICRYSTALING AGENT" should read --COSMETIC COMPOSITION COMPRISING A LIPID FRACTION FROM VEGETAL SOURCE AND ANTICRYSTALLING AGENT--.

In the claims:
Column 15, Claim 3,
Line 20, "about" should read --to--.

Signed and Sealed this
Fourth Day of November, 2014

Michelle K. Lee
*Deputy Director of the United States Patent and Trademark Office*